United States Patent [19]

Oprandy

[11] Patent Number: 5,039,493
[45] Date of Patent: Aug. 13, 1991

[54] POSITIVE PRESSURE BLOTTING APPARATUS WITH HYDROPHOLIC FILTER MEANS

[75] Inventor: John J. Oprandy, Rockville, Md.

[73] Assignee: The United States of America as represented by the Secretary of the Navy, Washington, D.C.

[21] Appl. No.: 519,072

[22] Filed: May 4, 1990

[51] Int. Cl.[5] .................. B01L 11/00; B01D 71/28
[52] U.S. Cl. ................................ 422/101; 422/100; 422/102; 435/300; 435/301; 210/224; 210/321.84; 210/500.42
[58] Field of Search ............... 435/300, 301; 422/100, 422/101, 102; 210/224, 321.84, 500.42

[56] References Cited

U.S. PATENT DOCUMENTS

| | | | |
|---|---|---|---|
| 4,317,726 | 4/1982 | Shepel | 422/101 X |
| 4,461,328 | 7/1984 | Kenney | 141/286 X |
| 4,493,815 | 1/1985 | Fernwood et al. | 422/101 |
| 4,797,259 | 1/1989 | Matkovich et al. | 422/101 |
| 4,853,335 | 8/1989 | Olsen et al. | 436/527 |
| 4,948,564 | 8/1990 | Root et al. | 422/102 X |

OTHER PUBLICATIONS

Collection of catalog pages, Feb. 1990?.
Am . J. Trop. Med. Hyg.; vol. 38, No. 1, pp. 181-186 (87-108) (1988).
J. Clin. Microbiology; pp. 74-77, (Jan. 1989).

Primary Examiner—Robert J. Warden
Assistant Examiner—Stephanie Blythe
Attorney, Agent, or Firm—A. David Spevack; William C. Garvert

[57] ABSTRACT

A positive pressure blotting apparatus having a bottom section, at least one middle section and a top section. A first volume of space is encompassed between the top section and the middle section. A positive pressure is maintained in the first volume of the apparatus. A second volume of space is encompassed between the middle section and the bottom section to capture eluate. An alignment means is used to align the top section to the middle section. A means is provided to apply positive pressure in the first volume. A hydropholic filter means for binding biological materials is positioned on or in the middle section, and a means is provided to secure the top, middle and bottom section together to form a pressure blotting apparatus.

13 Claims, 2 Drawing Sheets

POSITIVE PRESSURE BLOTTING APPARATUS WITH HYDROPHOLIC FILTER MEANS

BACKGROUND OF THE INVENTION

1. Field of the Invention

This invention relates to blotting test apparatus. More particularly this invention relates to a positive pressure blotting apparatus for biological molecules.

2. Description of the Prior Art

Blotting membrane based tests for biological samples have become common. The The tests are described in an article by Leary, *Proc. Natl. Acd. Sci. USA*, Vol 80, pp. 4045-4049, (1983). A standard apparatus for blotting or dot blotting onto membranes can be purchased can be purchased from many different suppliers. Each supplier appears to have a special design to accelerate filtration, avoid migration of test points, referred to as "cross-talk", and otherwise protect samples from contamination.

As the size of the biological molecule increases, greater difficulty is experienced in filtering the sample to bind the molecule to the filter material. In all of these devices, attempts are made to improve the filtration rate by applying negative pressure to the filter medium by creating a vacuum in the chamber under the filter medium.

Some in the prior art have suggested that applying positive or negative pressure are equivalent however, in all specific examples, negative pressure is used. Olsen, et al., in U.S. Pat. No. 4,853,335 describes using positive or negative filtration in a colloidal gold particle concentration immunoassay. Matkovich, et al., in U.S. Pat. No. 4,797,259, describes an improvement in "well-type" diagnostic plate devices in which the use of positive and negative pressure are considered to be equivalent. Matkovich suggests that in both cases it is necessary to wet the filter material. Normally hydrophobic membranes, such as polyvinylidene fluoride, must be made hydrophilic in order to operate in the Matkovich invention. Matkovich renders the polyvinylidene fluoride hydrophilic by washing with reagents such as methanol. Matkovich suggests that applying positive pressure upstream of the membrane is equivalent to applying negative pressure down-stream of the membrane, but Matkovich illustrates only the use of negative pressure. Nothing in Matkovich provides evidence which supports the allegation of equivalence.

Methanol and other reagents used to render a membrane hydrophilic can denature or otherwise change the biological molecules which the blotting technique seeks to recover or analyses. It is preferred to have an apparatus and technique which avoids using damaging or denaturing reagents.

SUMMARY OF THE INVENTION

Accordingly, an object of this invention is an apparatus which uses a "dry" membrane.

Another object of this invention is an apparatus which will efficiently bind biological molecules to a membrane.

Yet another object of this invention is an apparatus which forms a closed system capable of continues operation.

These and additional objects of the invention are accomplished by a positive pressure blotting apparatus having a bottom section, at least one middle section and a top section. A first volume of space is encompassed between the top section and the middle section. A positive pressure is maintained in the first volume of the apparatus. A second volume of space is encompassed between the middle section and the bottom section to capture eluate. An alignment means is used to align the top section to the middle section. A means is provided to apply positive pressure in the first volume. A filter means for binding biological materials is positioned on or in the middle section, and a means is provided to secure the top, middle and bottom section together to form a pressure blotting apparatus.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements. The representations in each of the figures is diagrammatic and no attempt is made to indicate actual scales or precise ratios. Proportional relationships are shown as approximations.

DESCRIPTION OF THE PREFERRED EMBODIMENTS

Figure 1:
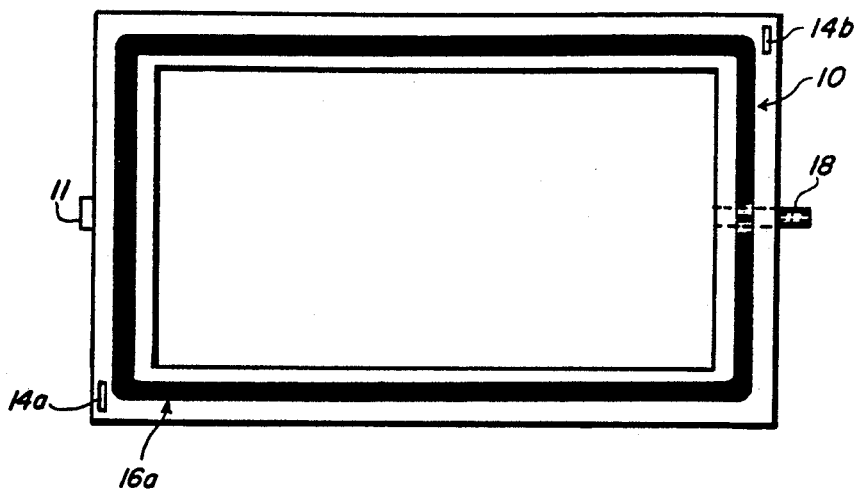
FIG. 1 is a top view of the top section of an embodiment of the apparatus.

Blotting devices are used to bind the biological molecule to a membrane. The membrane can take many forms which are well known in the art of making blotting apparatus. In a blotting apparatus, the membrane is immobilized by being trapped or clamped between a middle section and a bottom section. In an alternative version, the middle section is formed from more than one piece and the membrane is wedged between the parts of the middle section. The middle section also forms the guides or wells for multiple blot tests.

The apparatus of this invention works equally well with any number of wells from one upward. Most preferred are between 96 and 135 wells. The wells can be arranged in any manner. 135 wells can be arranged is three rows of 3×15 to facilitate cutting the membrane into three strips each having three rows and a tab for use in "dip-stick" tests. Various means can be used to clamp or hold the membrane in place.

There are many membranes which are well known for use in immobilizing biological molecules in these blotting test apparatus. Representative materials are listed in Matkovich referred to above and in catalogs for blotting systems. These membrane materials include nitrocellulose, cellulose based filaments, nylon, and polyvinylidene fluoride (PVDF). Many of the most desirable membrane materials are hydrophobic. Filtration through these materials is slow. It is common to try and improve the filtration by applying negative pressure to the down stream side of the membrane material by the usual techniques of vacuum filtration. In all the vacuum techniques, the membranes are made wettable or hydrophilic to facilitate the binding process.

In this invention, it was discovered that pressing biological molecules through a membrane has unexpected advantages over vacuum filtration. The advantages are particularly marked when the membrane is non-wettable and has a high bubble pressure. These high bubble pressure materials include polyvinylidene difluoride which is sold as Immobilon-P ®.

This invention imposes a positive pressure on the sample in the well pressing or forcing the sample through the filter material and membrane. In a vacuum filter apparatus vacuum pressure is dissipated over a portion of the membrane adjacent to the well. In a positive pressure apparatus, the well concentrates and directs the pressure to the top of the sample effectively pushing the sample through the membrane. Greater efficiency is achieved for the same power output to the pressure differential creating device such as a pressure pump or vacuum pump. Other pressure creating devices include syringes, motorized pumps, hand pumps, other piston powered pressure devices and compressed gas sources. Vacuum blotting through dry membranes or filters can not be achieved with a conventional vacuum technique.

The positive pressure causes another unexpected benefit. Positive pressure creates laminar flow through the membrane rather than the irregular or dispersed flow caused by a vacuum. The laminar flow reduces spread beyond the well boundaries on the down stream side of the membrane.

Having described the invention, the following is given to illustrate specific applications of the invention including the best mode now known to perform the invention. This illustration is not intended to limit the scope of the invention described in this application.

Figure 2:
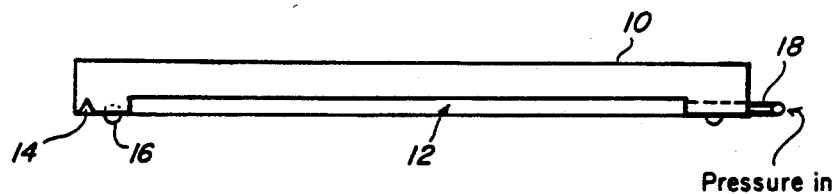
FIG. 2 is a side view of the top section of the apparatus illustrated in FIG. 1.
Figure 3:
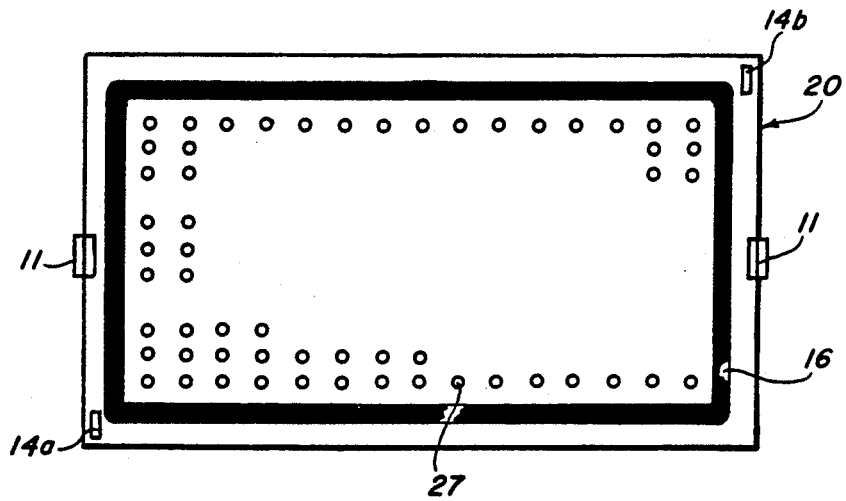
FIG. 3 is a top view of one embodiment of the middle section of the apparatus.

Referring to the drawings, FIG. 1 is a top view and FIG. 2 is a side view of the top section of the apparatus. In the embodiment illustrated, the top section 10 forms a hollow area or volume 12. Top section 10 serves as a manifold for pressurizing the apparatus. A conduit or tube 18 projects through the wall of the top section 10 through positive pressure can be applied to the hollow area 12. The top section 10 is mounted over a middle section 20 illustrated in FIG. 3 and 4. An alignment device 14a and b in the form of a triangular shaped post and socket assists in aligning all the well openings 27. An O-ring seal 16a is located about the periphery of the top section and in conjunction with the groove 16b forms a pressure seal. The seal should hold at least 20 psi gauge through much higher pressure is preferred. A device 11 secures the parts of the apparatus together and allows pressurization of the manifold top section 10.

Pressure is applied through conduit 18 through flexible tubing to a "Luer Lok" tip for a 50 ml or 100 ml syringe. The syringe will then be used to produce the desired pressure. This is a simple, low cost and preferred method. This syringe will produce between 30 and 60 psi at the membrane because of the low volume of the apparatus. In its preferred embodiment the apparatus is about the size of an ELISA plate. Of course, for larger apparatus alternate pressure sources can be compressed gas cylinders and pumps.

The middle section 20 can be of any design used for blotting tests. The section 20 contains wells 27 of approximately 0.2–0.3 mm in diameter and 1 cm in depth. This creates a well sufficient to hold approximately 250 $\mu$l of fluid in the well. Excess space or dead space in each well increases the pressure column above the fluid surface of the sample when pressure is applied to the manifold 10.

Figure 4A:
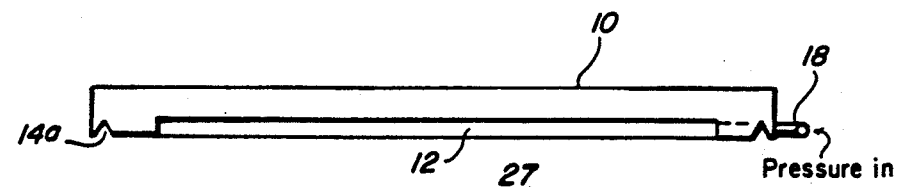
FIG. 4 is an exploded side view of an embodiment of the apparatus showing the relationship of the three major parts of this embodiment of the apparatus.
Figure 4B:

As shown in FIG. 4b, the well 27 extends through the middle section 20 and is preferably terminated in an O-ring 25a. The bottom section in the embodiment illustrated, contains a continuation of the well 27. An O-ring 25b is on the top surface of the bottom section 30. A membrane 22 is positioned between the sections 20 and 30. The O-rings 25a and b help to define the spot and keep the spot well defined. Alignment device 24a and b help to align section 20 and 30 so the wells 27 are aligned. In all cases, it is most preferred to have to membrane 22 sealed into position so that pressure or fluid does not dissipate around the membrane. The membrane can be sealed by clamping between two plates or between O-rings or gaskets or by any other means well known for these blotting devices.

A volume of space 33 in the section 30 is in communication with the down stream side of the wells 27 to collect the eluate. The space is in communication with conduit or tube 32 which is both an over flow to remove eluate and a means of applying negative pressure to the space 33.

Figure 4C:
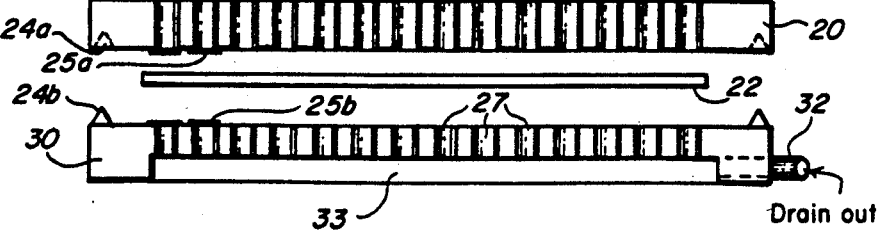
Figure 5:
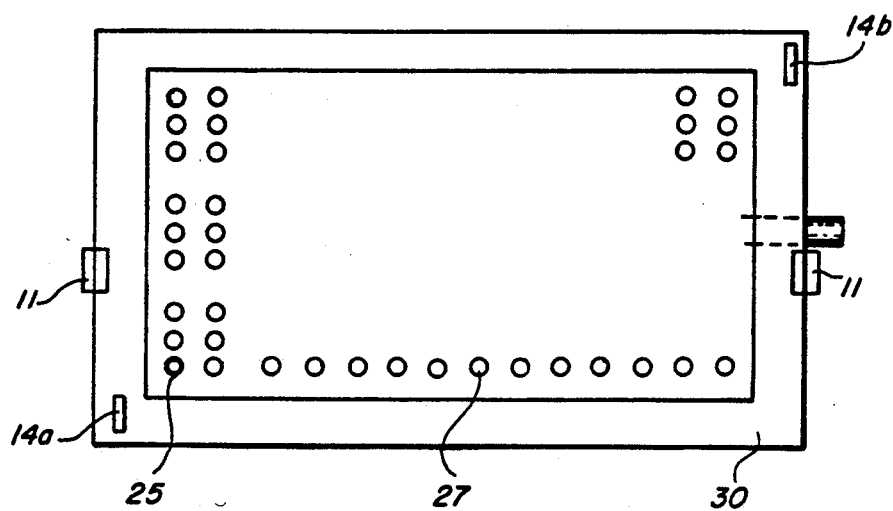
FIG. 5 is a top view of an embodiment of the bottom section of the apparatus.
Figure 6:
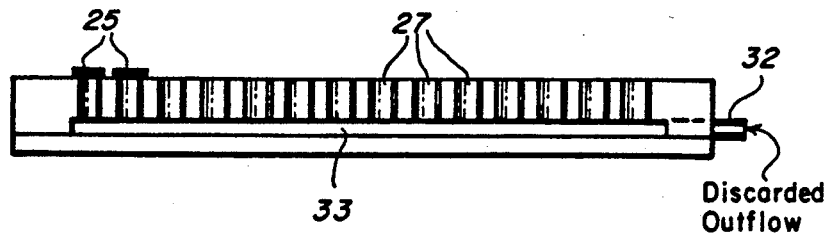
FIG. 6 is a side view of the embodiment of the bottom section of FIG. 5.

Referring to FIG. 4, the sections 20 and 30 are assembled together fixing a membrane 22 between them. Alternately the section 20 and be made of more than one piece and the membrane 22 can be fixed within the section 20. In such an embodiment, the section 30 can be in the form of a simple basin. There is no need to continue the wells 27.

It is preferred that the sections 10, 20 and 30 are fastened together strongly enough to withstand the greater than 20 psi pressure applied to manifold 10. A latch device 11 secures the sections together. This latch device can secure all three sections at once or it can secure the sections separately. The latch securing sections 30 to 20 should be strong enough to prevent the membrane 22 from moving so there is no "cross talk" between wells.

In an alternate embodiment the apparatus can be adapted to a closed circuit, automated system. In this embodiment, the sample wells are loaded in the normal manner with a ligand to be bound to the membrane. The manifold is secured and the assay is performed in a "flow-through" mode with the reagents being flowed through the membrane in successive steps. The manifold is adapted to provide the feed tubes for each well.

In the closed circuit mode, fluid flow can be in any direction and can be reversed at any time. Reversal of flow allows for efficient washing and the removal of entrapped reagents. Flow of reagent even slightly into the membrane allows for ligand bound in the deeper recesses to have material to react with. Any type of chemical, biological or diagnostic assay can be automated, enhanced and controlled in this way.

Obviously, many modifications and variations of the present invention are possible in light of the above teachings. It is therefore to be understood that, within the scope of the appended claims, the invention may be practiced otherwise than as specifically described.

What is claimed is:

1. A positive pressure blotting apparatus comprising a bottom section, at least one middle section and a top section, a first volume of space encompassed between said top section and said middle section for maintaining a positive pressure of at least about 30 psi in the first volume, a second volume of space encompassed between said middle section and said bottom section for capturing and disposing of eluate, an alignment means to align said top section to said middle section, a means to apply at least about 30 psi positive pressure in the first volume, a hydrophobic filter means for filtering and binding biological or chemical materials positioned and held on said middle section, and a means to secure said top, middle and bottom section together to form a blotting apparatus.

2. An apparatus according to claim 1 having a pressure tight seal positioned between said top and middle sections about the periphery of the sections.

3. An apparatus according to claim 2 wherein the pressure seal maintains a pressure of between about 30 and 60 psi gauge in said first volume.

4. An apparatus according to claim 1 wherein the filter means is a non-wettable, high bubble pressure, hydrophobic membrane.

5. An apparatus according to claim 4 wherein the filter means is selected from the group consisting of membranes of polyvinylidene difluoride, nitrocellulose and nylon.

6. An apparatus according to claim 3 wherein the filter means is a non-wettable, high bubble pressure, hydrophobic membrane.

7. An apparatus according to claim 6 wherein the filter means is selected from the group consisting of membranes of polyvinylidene difluoride, nitrocellulose and nylon.

8. An apparatus according to claim 1 wherein the pressure means is selected from the group consisting of syringe, motorized pump, hand pump, piston powered device, and compressed gas source.

9. An apparatus according to claim 8 wherein the pressure means is a syringe.

10. An apparatus according to claim 3 wherein the pressure means is selected from the group consisting of syringe, motorized pump, hand pump, piston powered device, and compressed gas source.

11. An apparatus according to claim 10 wherein the pressure means is a syringe.

12. An apparatus according to claim 9 wherein the filter means is polyvinylidene difluoride.

13. An apparatus according to claim 11 wherein the filter means is polyvinylidene difluoride.

* * * * *

UNITED STATES PATENT AND TRADEMARK OFFICE
CERTIFICATE OF CORRECTION

PATENT NO. : 5,039,493
DATED : August 13, 1991
INVENTOR(S) : John J. Oprandy

It is certified that error appears in the above—identified patent and that said Letters Patent is hereby corrected as shown below:

On the Title page, Item [54] and [57] should read as follows:

In the Title: "HYDROPHOLIC" should be "HYDROPHOBIC";

In the Abstract, line 10: "hydropholic" should be "hydrophobic";

Column 1, line 2: "HYDROPHOLIC" should be "HYDROPHOBIC";

Column 1, line 12: one "The" (second occurrence) should be deleted;

Column 1, line 15: one "can be purchased" should be deleted.

Signed and Sealed this

Twenty-fifth Day of May, 1993

Attest:

Attesting Officer

MICHAEL K. KIRK

Acting Commissioner of Patents and Trademarks